(12) United States Patent
Halloran

(10) Patent No.: US 6,272,877 B1
(45) Date of Patent: Aug. 14, 2001

(54) PERSONAL COOLING DEVICE AND METHOD

(75) Inventor: Daniel P. Halloran, Lakewood, OH (US)

(73) Assignee: Cobalt Entertainment, Incorporated, Lakewood, OH (US)

( * ) Notice: Subject to any disclaimer, the term of this patent is extended or adjusted under 35 U.S.C. 154(b) by 0 days.

(21) Appl. No.: 09/418,196

(22) Filed: Oct. 13, 1999

(51) Int. Cl.[7] .................................................. F25D 23/12
(52) U.S. Cl. ............................................... 62/259.3; 62/77
(58) Field of Search ................................. 62/259.3, 420, 62/425, 530

(56) References Cited

U.S. PATENT DOCUMENTS

| 4,405,348 | 9/1983 | Pasternack . | | |
|---|---|---|---|---|
| 4,459,822 | 7/1984 | Pasternack . | | |
| 5,027,807 | 7/1991 | Wise et al. . | | |
| 5,092,129 | 3/1992 | Bayes et al. . | | |
| 5,111,668 | 5/1992 | Parrish et al. . | | |
| 5,113,666 | 5/1992 | Parrish et al. . | | |
| 5,193,347 | * 3/1993 | Apisdorf | ................................. | 62/3.7 |
| 5,327,585 | * 7/1994 | Karlan | ......................................... | 2/7 |
| 5,655,374 | * 8/1997 | Santilli et al. | .......................... | 62/3.5 |
| 5,715,533 | * 2/1998 | Stein | ............................................ | 2/7 |

FOREIGN PATENT DOCUMENTS 3531-407A   * 3/1987   (DE) .................................... 62/259.3

* cited by examiner

Primary Examiner—William Doerrler
Assistant Examiner—Melvin Jones
(74) Attorney, Agent, or Firm—Fay, Sharpe, Fagan, Minnich & McKee, LLP

(57) ABSTRACT

The device includes an air intake channel, a vacuum source, a cooling means, and a cool air distribution channel. Ambient air is brought into contact with the cooling means and cool air is distributed to desired areas. Cooling of the person may also be achieved by virtue of indirect contact with the cooling source. The device and method are particularly suited to provide comfort to a person wearing a costume or mask.

24 Claims, 11 Drawing Sheets

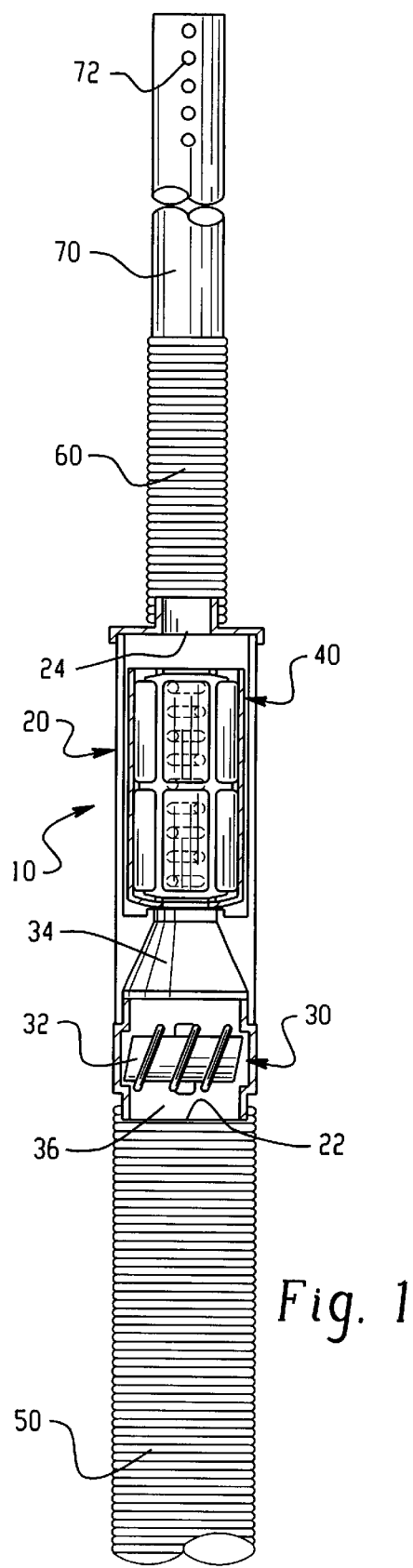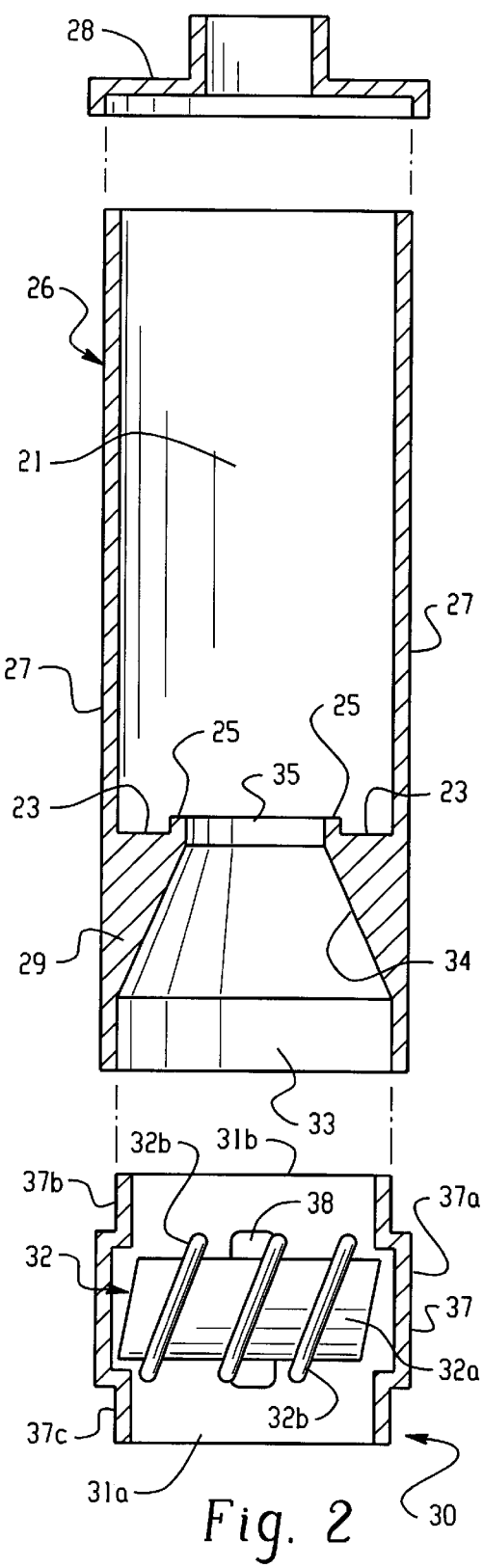
Fig. 1
Fig. 2

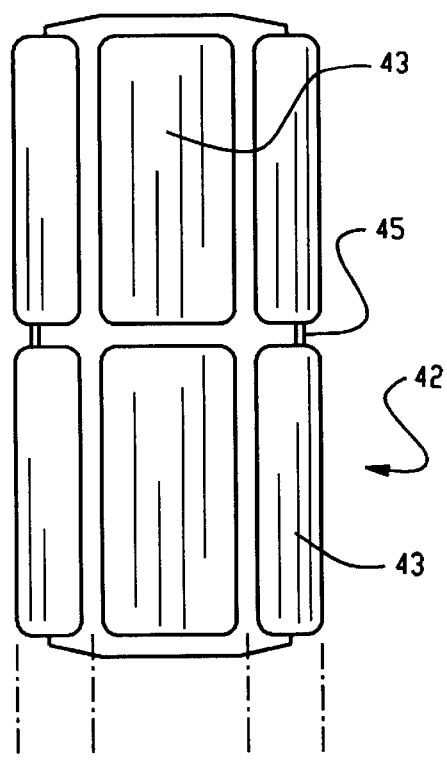
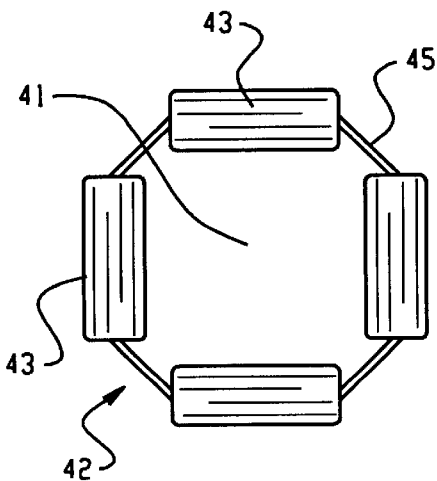
Fig. 4
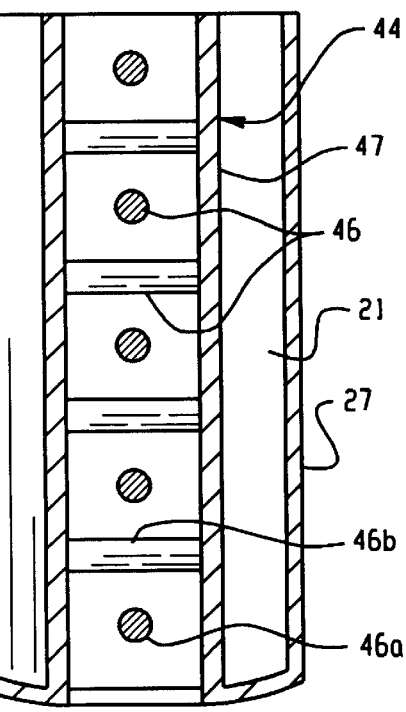
Fig. 3
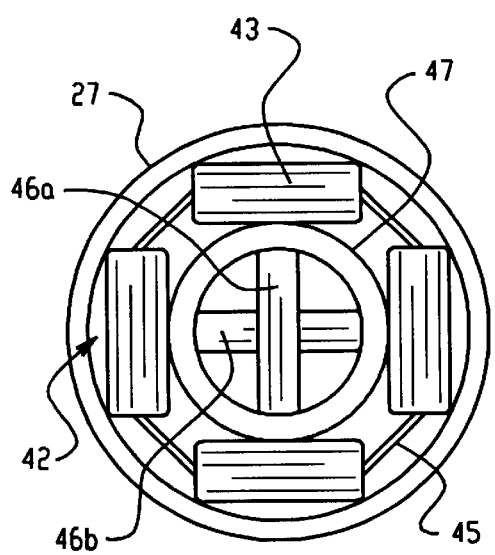
Fig. 5

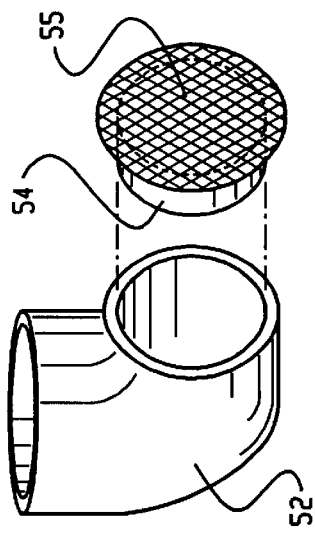
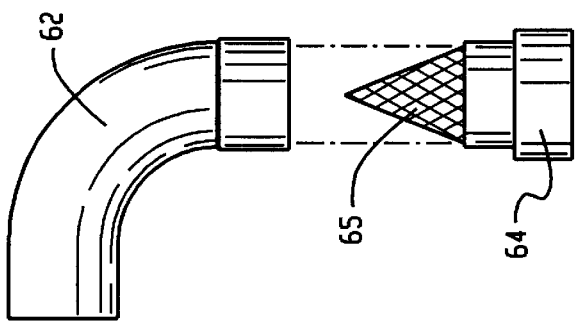
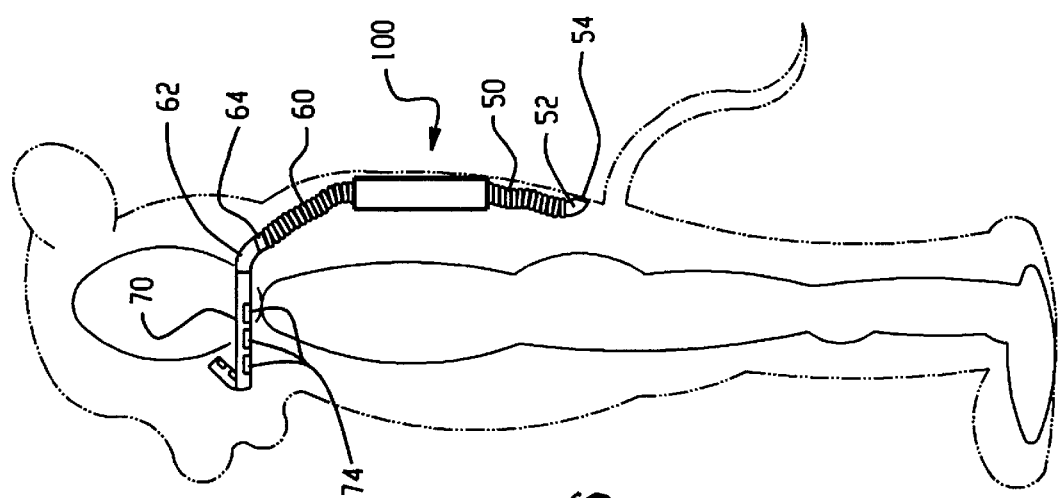

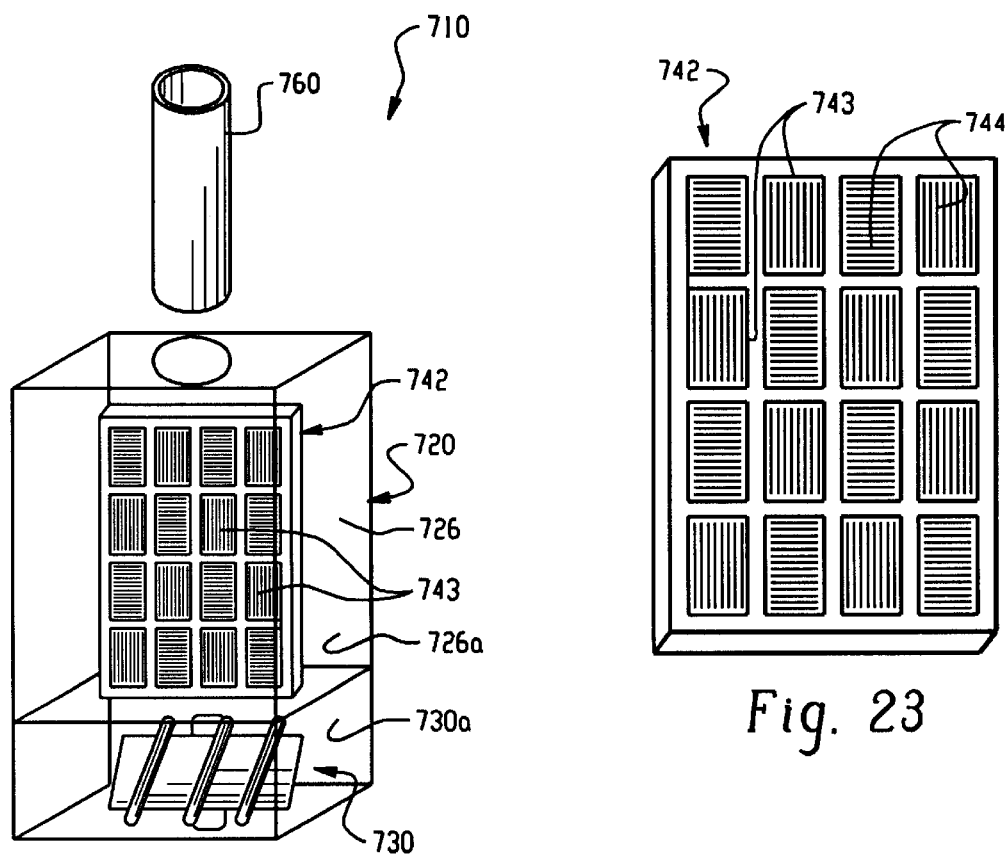
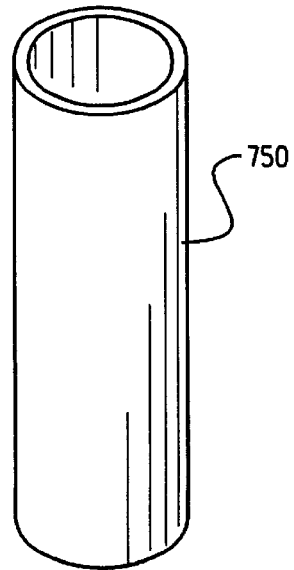
Fig. 22
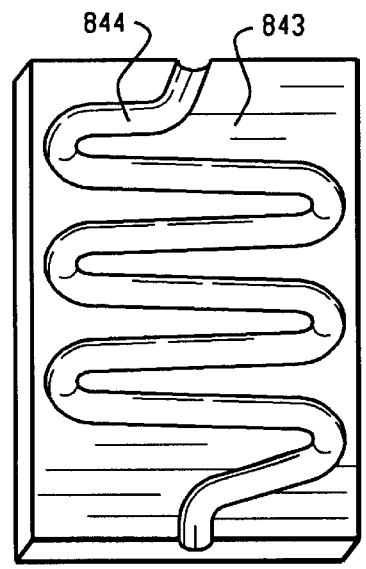
Fig. 23
Fig. 24

PERSONAL COOLING DEVICE AND METHOD

BACKGROUND OF THE INVENTION

1. Field of the Invention

This invention relates to portable air conditioning devices and more particularly to a device for cooling a person wearing a costume, mask, or other clothing.

2. Related Background Art

Costumes and masks are worn for a variety of purposes, including for celebrations, entertainment, or promotion. For example, people wear costumes and masks for holidays such as Halloween, Mardi Gras, and Christmas as well as for themed occasions. Entertainers and entertainment organizations also use costumes and masks for theatrical presentations, strolling entertainment, and telegram-style entertainment for groups or individuals. Further, many theme parks, restaurants, casinos, and other recreational facilities use costumes and masks to entertain their patrons and guests. Finally, costumes and masks are used to promote products, companies, schools, and other institutions.

In the United States alone, there is a vast number of mask and costume manufacturers and retailers. In addition, craft, fabric, and sewing supply outlets throughout the country provide materials for individuals to construct their own mask or costume.

Traditional costumes and masks share a similar flaw in that the materials and design needed to create the desired effect or illusion results in an uncomfortable and sometimes unsafe environment for the wearer. More specifically, traditional costumes are poorly ventilated and the wearer can experience extreme discomfort, especially when the surrounding temperature is warm.

There are several prior art devices that attempt to solve this problem. A mascot-style costume traditionally uses a molded, hardened material such as fiberglass for its head structure, which is then covered with fur or material. The eyes and mouth in the head of a mascot-style costume are usually made of a screen material to allow the wearer to see out and let air in.

One known means of combating the discomfort caused by wearing a mascot-style costume is to install a fan inside the head of the costume. The fan circulates air inside the head and cools the user by drying perspiration on the wearer's face. However, this prior art solution to the problem introduces little fresh air into the costume and any comfort initially provided is generally short lived.

Alternatively, a fan can be mounted in an opening in the mascot head. To maintain the aesthetic quality of the costume, the opening is usually located on the top or back of the head. The direction of the airflow depends on the placement of the fan. If the airflow is directed inwardly, the fan's placement limits the flow of fresh air in the proximity of the wearers nose and mouth. If the airflow is directed outwardly, it will draw in fresh air through the eye and mouth holes of the costume, but a very small fan is needed in that mode to avoid undue noise and preserve the illusion created by the custom. Under these circumstances, the resulting air movement caused by the fan is so limited and diffused that it provides little comfort for the wearer. In either mode, the degree of comfort experienced by the costume wearer is dependent on the surrounding air temperature.

Another drawback of the foregoing devices is that they require a rigid mascot-style head for mounting. Moreover, these devices do not do anything to reduce the wearer's internal body temperature.

There are devices available to lower a person's internal body temperature. One such device uses the physics of condensation and evaporation to extract heat from a person's body. Specifically, metal plates are spaced apart, one of which is in contact with the back of the wearer's neck. The plates are moistened with a damp, sponge-type material and then the condensation is evaporated with the use of a small fan. This method is not effective inside of a costume, however, because the humidity developed remains inside the costume. This results in discomfort and possible damage to the costume.

Other known devices for lowering a person's body temperature are the cold wrap and cold vest. The cold wrap is brought into indirect contact with the neck, and the cold vest comes into contact with the chest and back. The gel paks are covered with insulating fabric or material to prevent frostbite and also to provide a wearable item for the user. A disadvantage of these devices is that they concentrate the cooling in isolated areas.

Another device for reducing internal body temperature is a circulatory vest or suit. This device uses a long hose, which is serpentined throughout the outfit, and a battery-powered pump to circulate water through the hose. The water is cooled by passing through a reservoir containing ice. This device is often used for quadriplegics as it provides distributed cooling of the body. Although a portable model is available for costume purposes, its noise level and high cost of production precludes its use in the costume and entertainment field.

Another device used to reduce internal body temperature employs a portable, Freon®-based air conditioner. These devices have their principle application in astronaut suits. The size, noise, weight, and cost of these devices makes them impractical in the costume or entertainment field.

Therefore, a need exists for a device and method of cooling a costume or mask that can deliver comfort in a light and compact package and without compromising the desired effect of the costume.

SUMMARY OF THE INVENTION

The subject invention has each of the foregoing advantages and more. In a preferred embodiment, a personal cooling device is provided. The device includes a vacuum source in fluid communication with an air intake channel for drawing ambient air into the device. Means for cooling the ambient air drawn into the intake channel are also provided, with the cooling means being in fluid communication with the input channel. Finally, the device includes a cool air distribution channel for distributing cooled air in the vicinity of the person.

A new method for cooling a person is also provided. The method includes the steps of drawing in ambient air through an intake channel; cooling the air below ambient temperature by means of a cooling source in fluid communication with the intake channel; and delivering the cooled air in a desired area adjacent the person to provide comfort. In an alternative embodiment, the method includes the step of placing the cooling source in indirect contact with the person.

It is an object of the subject invention to provide a device and method for providing comfort to a person wearing a costume, mask, or visor. A further object of the invention is to provide a device and method that cools a person with fresh air. These and other objects and advantages of the subject invention will become more apparent and fully understood from the detailed description of the invention in conjunction with the accompanying drawings.

BRIEF DESCRIPTION OF THE DRAWINGS

The present invention exists in the construction, arrangement, and combination of various parts of the device, specifically defined by the claims and illustrated in the accompanying drawings.

FIG. 1 is an elevational view in partial section of a preferred embodiment of the cooling device of the present invention adapted for a costume;

FIG. 2 is an exploded elevational view of the cooler and fan unit of the device of FIG. 1 shown in partial section;

FIG. 3 is an exploded elevational view of the preferred cooling unit assembly according to the present invention;

FIG. 4 is a top plan view of the gel pak insert shown in FIG. 3;

FIG. 5 is a top plan view of the cooling unit assembly shown in FIG. 3;

FIG. 6 is a side elevational view of a device according to the present invention that is attached to a costume;

FIG. 7 is a perspective view of the intake elbow and fitting shown in FIG. 6;

FIG. 8 is a front elevational view of a hands-free connector and output elbow shown in FIG. 6;

FIG. 22 is an exploded view of some of the components of another embodiment of the device according to the subject invention;

FIG. 23 is a perspective view of an alternative gel pak insert for use in a device according to the subject invention;

FIG. 24 is a perspective view of another alternative gel pak insert for use in a device according to the subject invention;

DETAILED DESCRIPTION OF THE INVENTION

Figure 10:
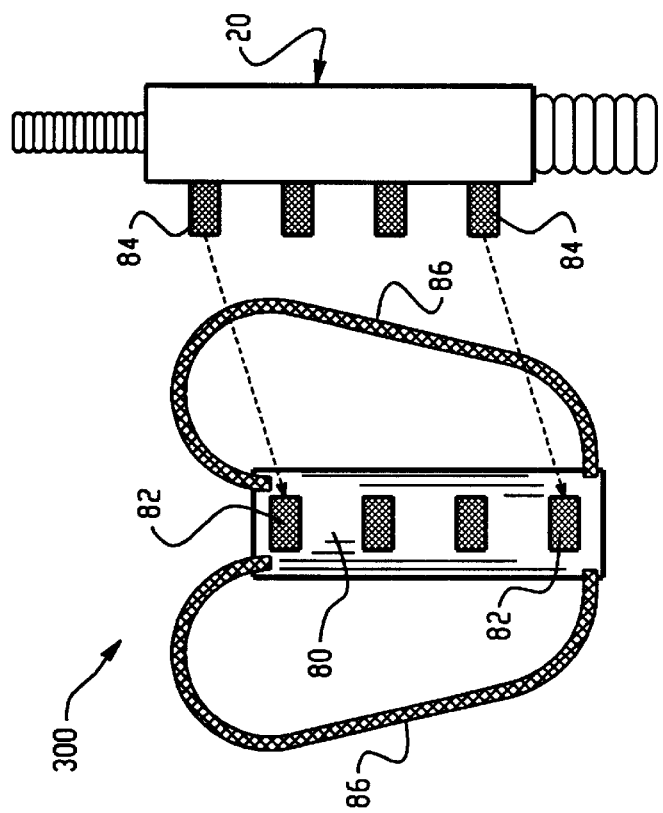
FIG. 10 is a partially-exploded rear elevational view of another embodiment of the device according to the present invention.

A preferred embodiment of a device according to the present invention for use in a costume is shown in FIG. 1 as device 10. Device 10 generally comprises a cooler and fan unit 20, an intake hose 50, an output hose 60, and a distribution hose 70. These elements function in combination to draw ambient air into the cooler and fan unit 20 through the intake hose 50, cooling the air below ambient temperature by means of a cooling device in fluid communication with the intake channel, and delivering the cooled air via distribution hose 70 to a desired area adjacent the costume wearer to provide comfort. The details of the components of device 10 are provided below.

With further reference to FIG. 2, cooler and fan unit 20 houses the air cooling and delivery means necessary to operate device 10. Cooler and fan unit 20 is comprised of three concentric and preferably lightweight plastic sections that are fastened together, namely core housing 26, lid 28, and fan assembly 30. Core housing 26 comprises a hollow exterior cylinder 21 having a cylindrical wall 27, a bottom surface 23, and lips 25 extending upwardly therefrom. The outside diameter of the cylinder 21 is substantially the same as the inside diameter of lid 28. Concentric with exterior cylinder 21 is nozzle 34, which is integrally formed within lower portion 29 of core housing 26. Nozzle 34 has an opening 33 in the lower portion 29 and an outlet 35 between lips 25.

Contained within cooler and fan unit 20 are fan assembly 30 and cooling unit assembly 40. Fan assembly 30 includes a fan housing 37 comprising a central section 37a, an upper section 37b, and a lower section 37c. These sections are integrally formed hollow tubes of varying diameters; specifically, the central section 37a is of a slightly greater diameter than the diameter of upper and lower sections 37b and 37c, which are substantially the same. The outside diameter of upper section 37b is substantially the same as the inside diameter of opening 33 so as to provide an interference fit between the core housing 26 and fan assembly 30.

Fan or impeller 32 comprising a center shaft portion 32a and vanes 32b extending therefrom is mounted on a spindle 38 for rotational movement within central section 37a of fan housing 37. The longitudinal axis of center shaft portion 32a is perpendicular to the longitudinal axis of fan housing 37, and vanes 32b of impeller 32 are disposed at an angle from the longitudinal axis of the center shaft portion 32a. The fan assembly further includes a fan inlet 31a in the lower section 37c and a fan outlet 31b in the upper section 37b. The energy source for the fan is most preferably two batteries that form part of an electronic circuit having a series to parallel switch, which enables the fan to operate at multiple speeds.

Cooling unit assembly 40 is contained within core housing 26 and provides the means for cooling air drawn into device 10 by fan assembly 30. A preferred embodiment of cooling unit assembly 40 is shown in FIGS. 3–5. It is comprised of gel pak insert 42, interior cylinder 44 having a cylindrical wall 47, and a plurality of temperature conducting rods 46. As used in this specification, a gel pak insert means a container for storing a non-toxic, gelatinous liquid that has been chilled or frozen. In this embodiment, gel pak insert 42 includes a plurality of cells 43 containing the liquid, which cells are joined together in a predetermined arrangement with strands 45, forming an opening 41. Gel pak insert 42 is positioned between wall 27 and wall 47 of interior cylinder 44 and seated on bottom surface 23 of core housing 26. Gel pak insert 42 thus provides the cooling source in this embodiment of the invention.

As shown in FIGS. 3 and 5, temperature conducting rods 46 are positioned within interior cylinder 44 in a stacked arrangement. Specifically, the bottom rod 46a in the stack is oriented perpendicular to the rod 46b directly above it, and that arrangement continues for the remaining rods in the stack. Temperature conducting rods 46 are preferably made of an efficient temperature conducting material such as aluminum or, alternatively, liquid-filled rods. The ends of the rods are in contact with the cylindrical wall 47, which contact provides vertical support for the rods.

Cooler and fan unit 20 is assembled by securing lid 28 to wall 27 of core housing 26 (containing cooling unit assembly 40) and inserting upper section 37b of fan assembly 30 into opening 33 of the lower portion 29 of core housing 26. Similarly, intake hose 50 is securely coupled to the lower section 37c of fan assembly 30, output hose 60 is securely coupled to the upper portion of lid 28, and distribution hose 70 is securely coupled to output hose 60 by conventional means (not shown). Intake hose 50 and output hose 60 are preferably made from flexible, corrugated plastic material that is capable of relatively sharp bending angles, while distribution hose 70 is made of a cloth fabric and contains air distribution holes 72 at the upper end thereof. As one skilled in the art will appreciate, the foregoing hose connections must be well sealed for device 10 to operate properly.

FIG. 6 shows a device 100 according to the subject invention attached to a costume. In this embodiment, a hollow intake elbow 52 is connected to intake hose 50 on one end and a hollow fitting 54 on the other. With further reference to FIG. 7, fitting 54 has a screen 55 secured to it in a conventional way. The outside surface of screen 55 is secured within an opening in the costume (not shown) such that it is substantially flush with the outside surface of the costume. Similarly, as shown in FIG. 8, a hands-free connector 64 having a conical filter 65 joins a hollow output elbow 62 to output hose 60. In turn, distribution hose 70 is coupled to output elbow 62 and is secured to the costume by a plurality of velcro tabs 74 arranged in a spaced relationship along distribution hose 70. As one skilled in the art will appreciate, each such velcro tab 74 has two mating components (not shown), one secured to distribution hose 70 and the other to the costume.

Figure 9:
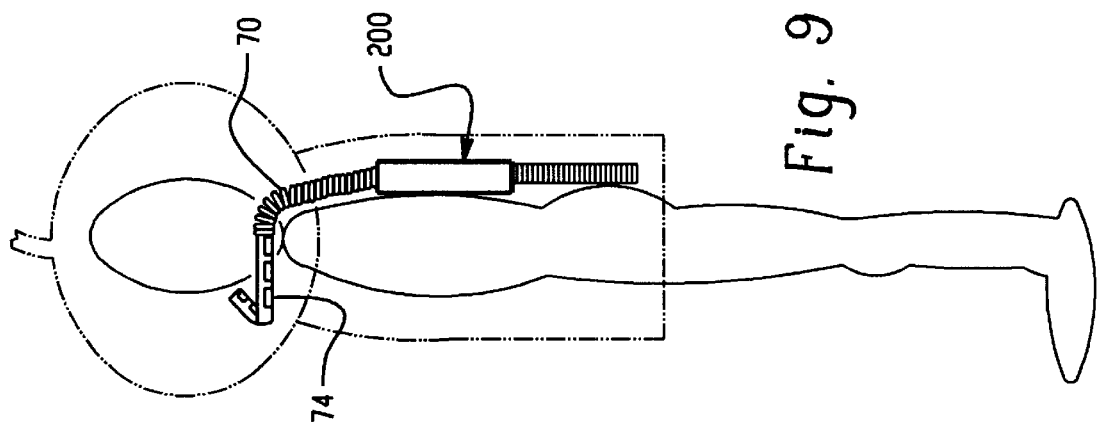
FIG. 9 is a side elevational view of another embodiment of the device of the present invention.

FIG. 9 illustrates another embodiment of the device according to the present invention. Device 200 is substantially the same as the device of FIG. 1 except that distribution hose 70 is secured to an inside surface of the costume through the use of velcro tabs 74 as in FIG. 6.

Another embodiment of the device according to the present invention as shown in FIG. 10 is device 300. In this embodiment, cooler and fan unit 20 is secured to attachment pad 80 by mating velcro tabs 82, 84 and the attachment pad 80 is in turn removably secured to shoulder straps 86. Thus, unlike the embodiments of FIGS. 6 and 9, the cooling apparatus in this embodiment would be directly supported by the user.

Figure 11:
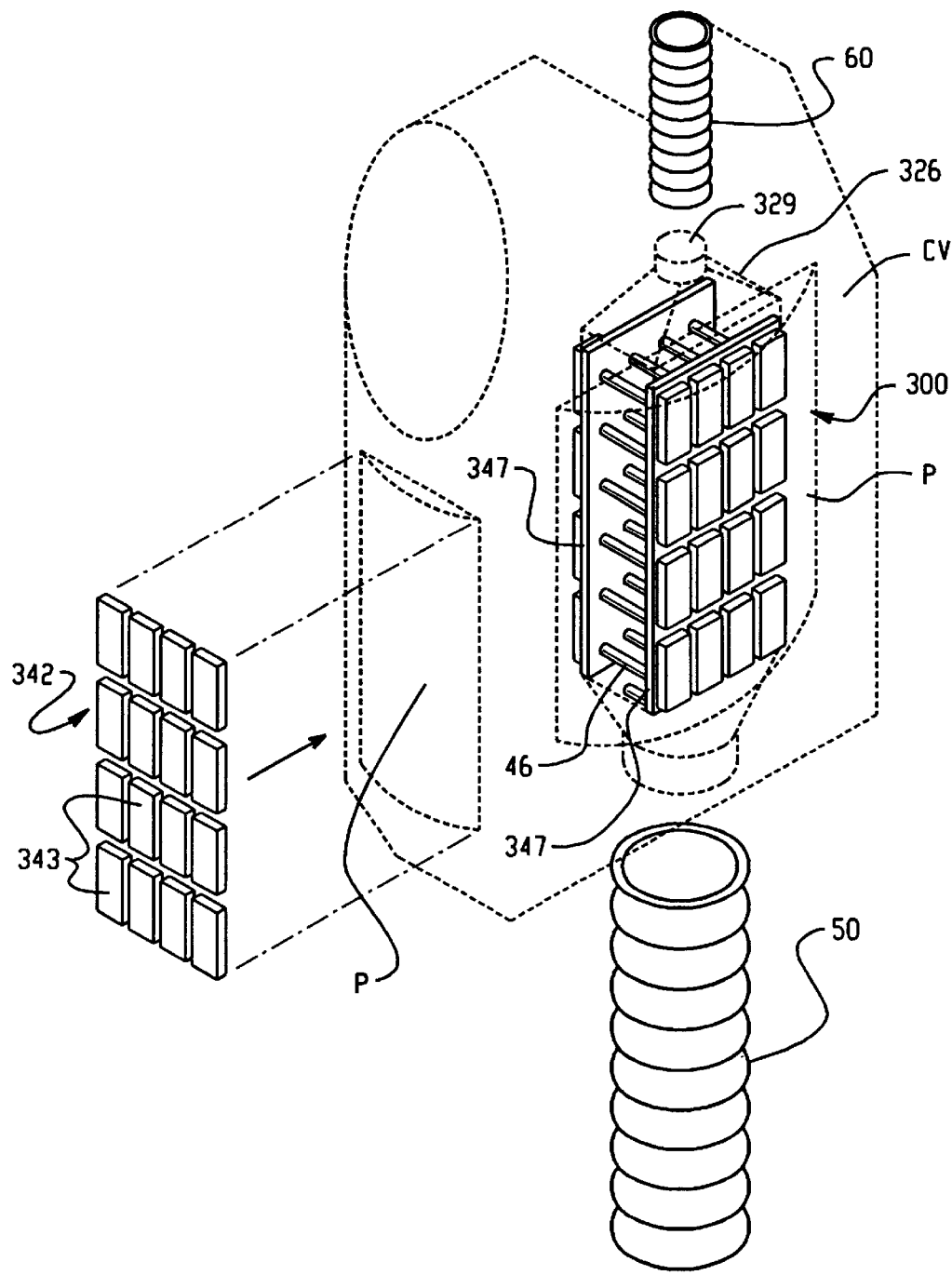
FIG. 11 is a partially-exploded perspective view of another embodiment of a device according to the invention.
Figure 12:
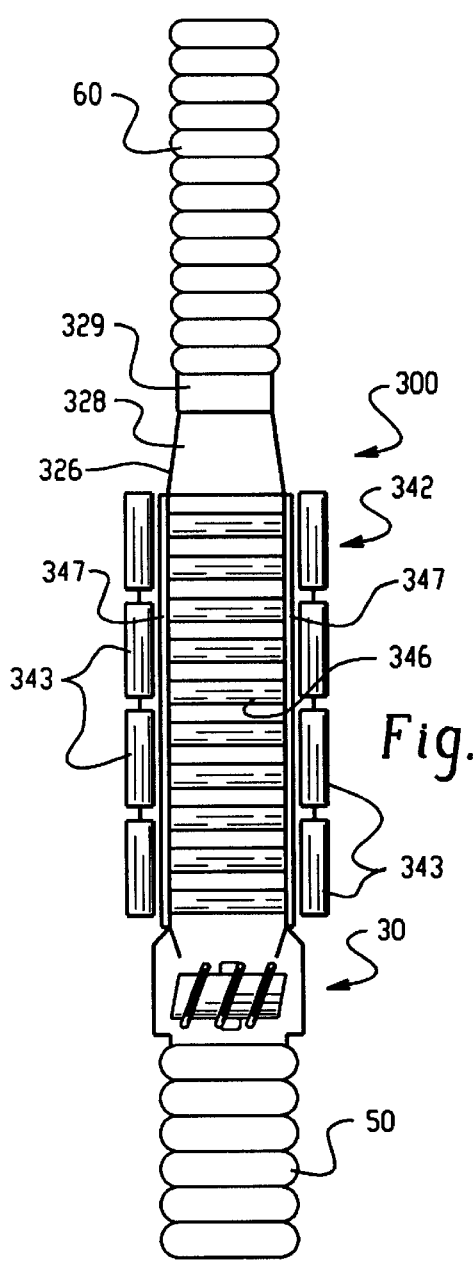
FIG. 12 is a side elevational view of the device shown in FIG. 11.
Figure 15:
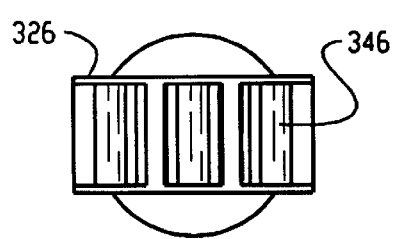
FIG. 15 is a top plan view of the core housing of FIG. 12.
Figure 13:
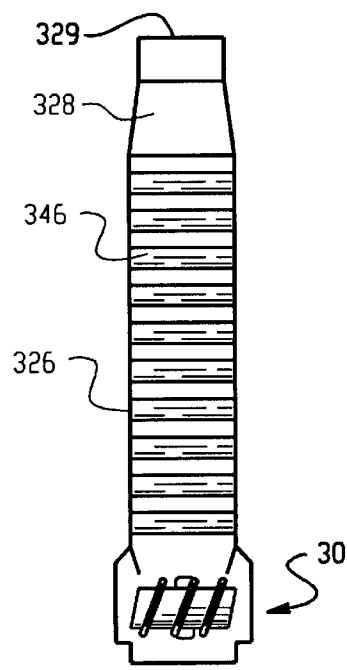
FIG. 13 is a side elevational view of the core housing of the device according to FIG. 11.
Figure 14:
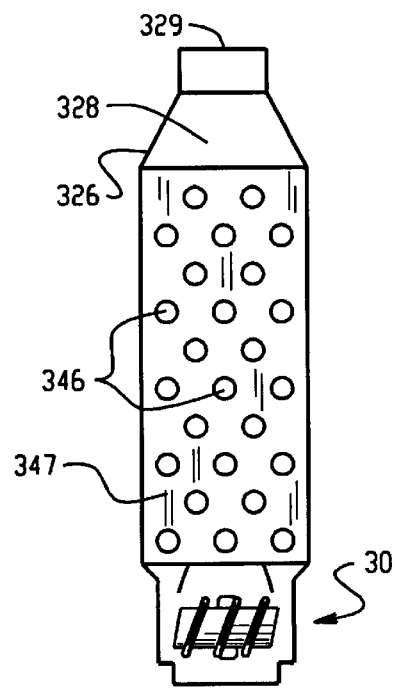
FIG. 14 is a front elevational view of the core housing shown in FIG. 13.

FIG. 11 shows another embodiment of the invention that may be used in connection with a cold vest (CV). The cold vest (CV) has a plurality of pockets (P) for holding device 300 and additional gel pak inserts 342, which are comprised of an array of rectangular cells 343. When the cold vest (CV) is worn by a user, at least some of the gel pak inserts 342 are in indirect contact with the body of the user, the separation distance being the thickness of the cold vest. It is envisioned that this embodiment would have applications outside of the entertainment realm, including backpacking.

With further regard to FIGS. 12–15, device 300 is comprised of intake hose 50, output hose 60, core housing 326, and fan assembly 30. Core housing 326 has an integrally molded top portion 328 with a central opening 329 around which one end of the output hose 60 is secured. Temperature conducting rods 346 are mounted perpendicular to the longitudinal axis of the core housing 326 in a series of rows. The rows of temperature conducting rods 346 are separated from one another by temperature conducting plates 347 having openings to receive the ends of each temperature conducting rod 346.

Figure 16:
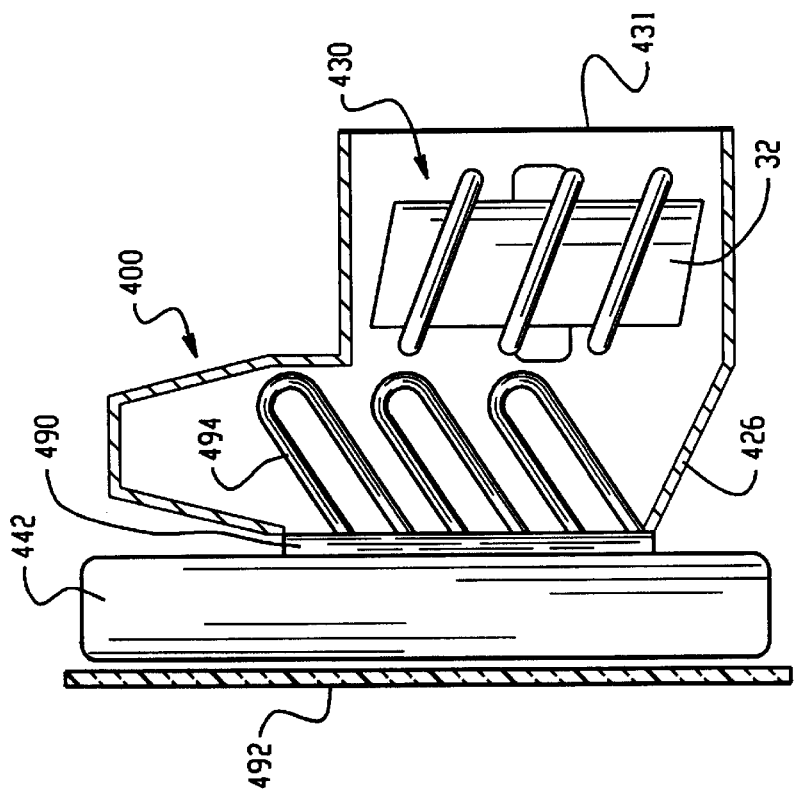
FIG. 16 is a sectional view of another embodiment of a device according to the subject invention.

The subject invention is also adapted for use with a head unit or mask. The embodiment shown in FIG. 16 is a device 400 that is preferably positioned at the base of the back of the head or mask. Device 400 is comprised of a fan assembly 430; core housing 426 comprising a plurality of temperature conducting coils 494; gel pak 442; cold bridge 490; and insulating fabric 492. In this embodiment, ambient air is drawn into core housing 426 through intake opening 431 by impeller 32. The air molecules then come into contact with temperature conducting coils 494, which cool the air molecules because the coils are at a lower temperature by virtue of their thermal communication with gel pak 442 via cold bridge 490. The cold bridge and conducting rods are preferably made of thermally conductive material such as aluminum.

Figure 17:
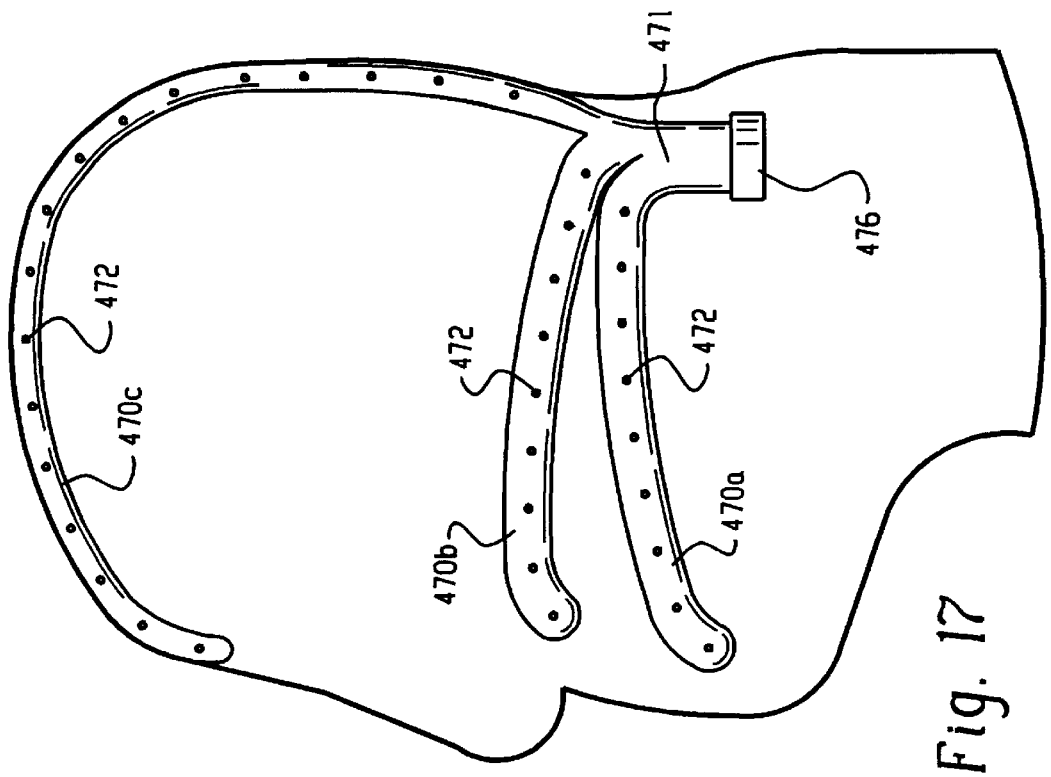
FIG. 17 is a sectional view of a head mask adapted for use with the device of FIG. 16.
Figure 19:
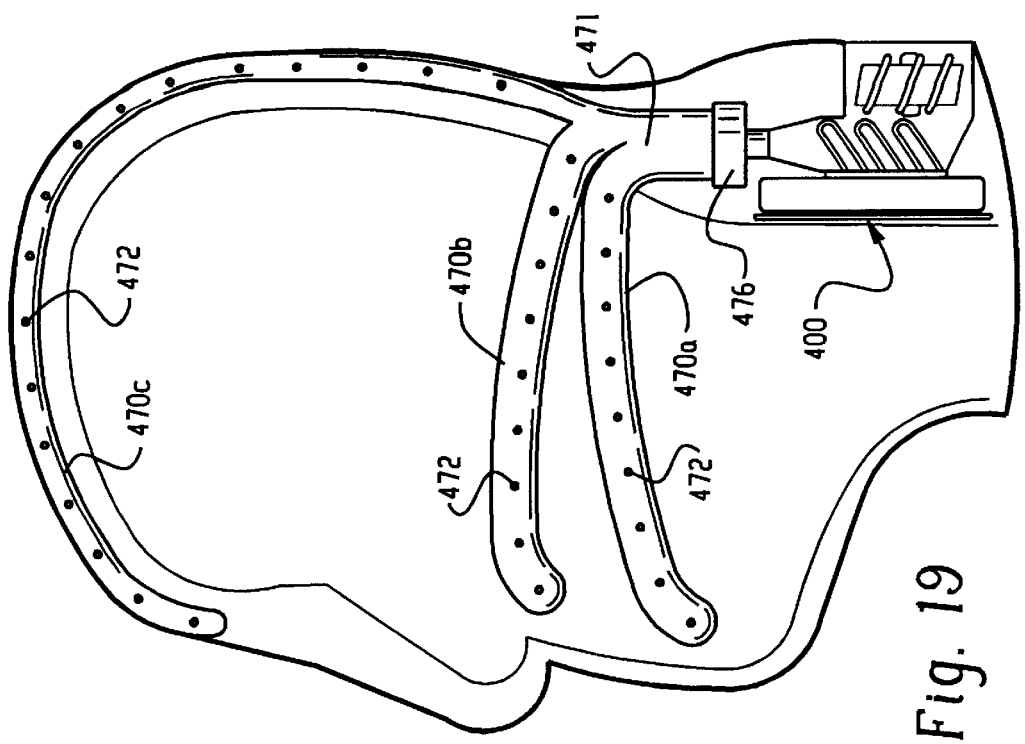
FIG. 19 is a side elevational view of the device shown in FIG. 18 installed in a mask.
Figure 18:
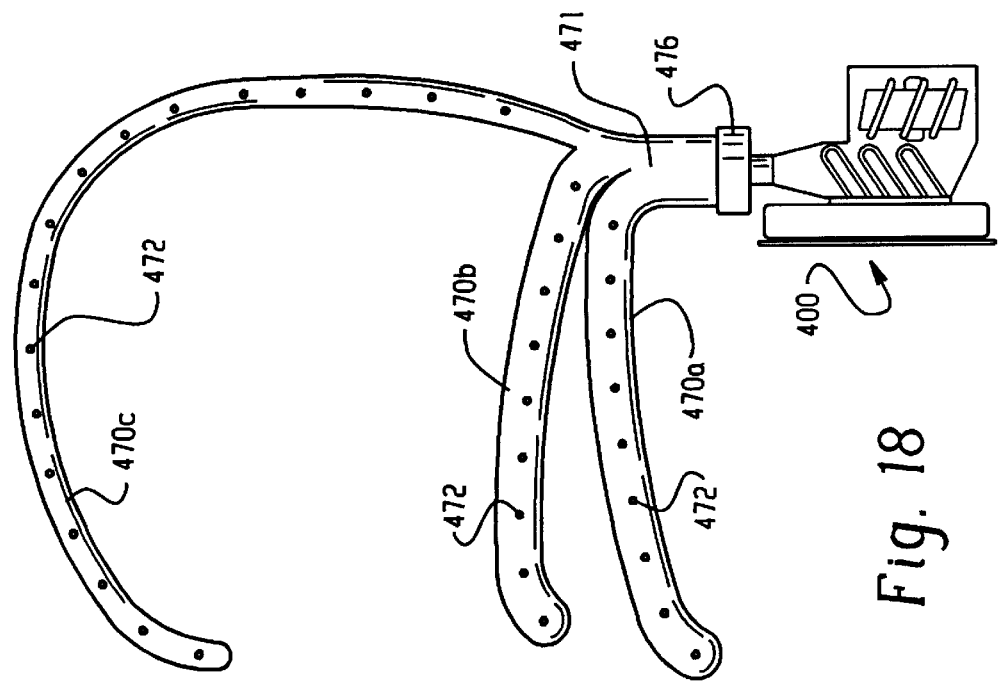
FIG. 18 is a side elevational view of another embodiment of a device according to the subject invention.

As shown in FIGS. 17–19, device 400 can be secured to a plurality of air distribution hoses 470a, 470b, and 470c through a connector ring 476. Connector ring 476 is coupled to a junction 471 formed by the interconnection of hoses 470a, 470b, and 470c. These hoses have a plurality of air distribution holes 472 though which cool air is introduced in the mask or head unit at various locations.

Figure 20:
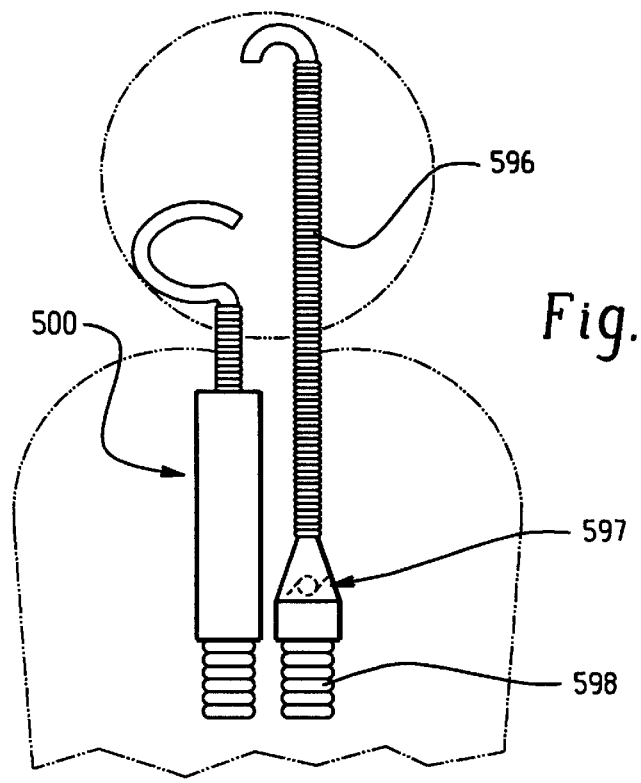
FIG. 20 is a schematic view of another embodiment of the device according to the subject invention.
Figure 21:
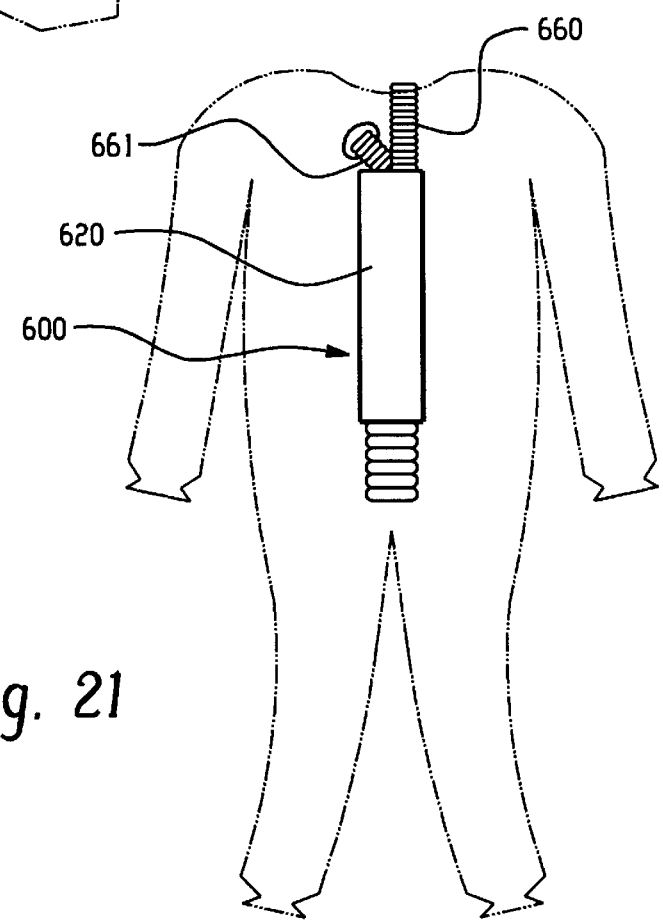
FIG. 21 is a schematic view of yet another embodiment of the device according to the subject invention.

Further embodiments of the device according to the subject invention are shown in FIGS. 20 and 21. FIG. 20 shows a device 500 substantially the same as device 10 except that it also provides for warm air removal from the costume. More particularly, warm air is removed from the costume head by drawing air through a warm air intake hose 596 through exhaust fan 597 and out of the costume through warm air output hose 598. Likewise, FIG. 21 shows a device 600 similar to device 10 except that it is adapted to be used with a cool air suit. This type of suit is worn under costumes and allows for circulation of cool air over the wearer's entire body. This is accomplished through a plurality of cool air output hoses 660 and 661 that extend from a junction (not shown) at the outlet of cooler and fan unit 620.

FIG. 22 illustrates yet another embodiment of a device according to the present invention. In this embodiment, device 710 comprises a cooler and fan unit 720 and intake hose 750 and output hose 760. Each of these components is preferably formed from closed-cell foam rubber that has a latex coating. Cooler and fan unit 720 comprises a gel pak chamber 726 and fan compartment 730 in fluid communication with gel pak chamber 726.

Cooler and fan unit 720 also comprises a lid (not shown) preferably constructed of a thinner closed-cell foam rubber, which lid covers gel pak chamber 726 and fan compartment 730. This construction provides the wearer with the option of placing the lid side of device 710 against his body or the relatively thicker back walls 726a and 730a of gel pak chamber 726 and fan compartment 730. The former option provides for greater thermal conductivity than the latter, but the construction is such that frostbite is avoided with both options.

To achieve the cooling effect in device 710, the gel pak chamber 726 contains a gel pak 742 formed in a rectangular pattern and comprising of a plurality of cells 743. With further reference to FIG. 23, cells 743 have a plurality of integrally formed ribs 744 designed to generate turbulence as air flows over them. Alternatively, this effect can be achieved by molding a serpentine channel 844 in the face of cell 843, as shown in FIG. 24. In either embodiment, the turbulence created has the effect of more even heat transfer between the gel pak and the air molecules passing over the gel pak.

Figure 25:
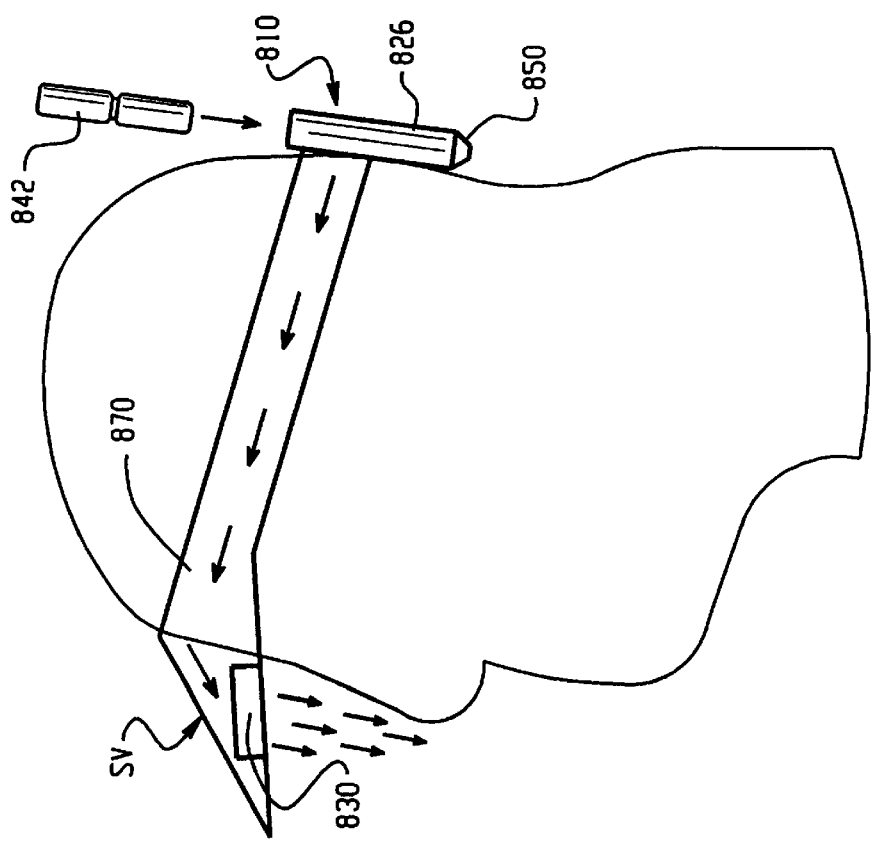
FIG. 25 is a side elevational view of a visor incorporating another embodiment of the device according to the subject invention.

Another embodiment of the device according to the subject invention is shown in FIG. 25, adapted to a sun visor (SV). Device 810 comprises an air intake channel 850, core housing 826 containing gel pak insert 842, distribution channel 870 contained within sun visor (SV), and fan 830, all of which are in fluid communication with one another. Ambient air molecules drawn into device 810 by fan 830 come into contact with gel pak insert 842, causing the air to be cooled below ambient temperature. This cool air is conveyed through distribution channel 870 and discharged by the fan 830 located in the visor to cool the wearer's face. Moreover, device 810 also cools the wearer's head by contact with the distribution channel 870 and core housing 826. These qualities make this device ideal for outdoor usage in places such as beaches or amusement parks.

Figure 26:
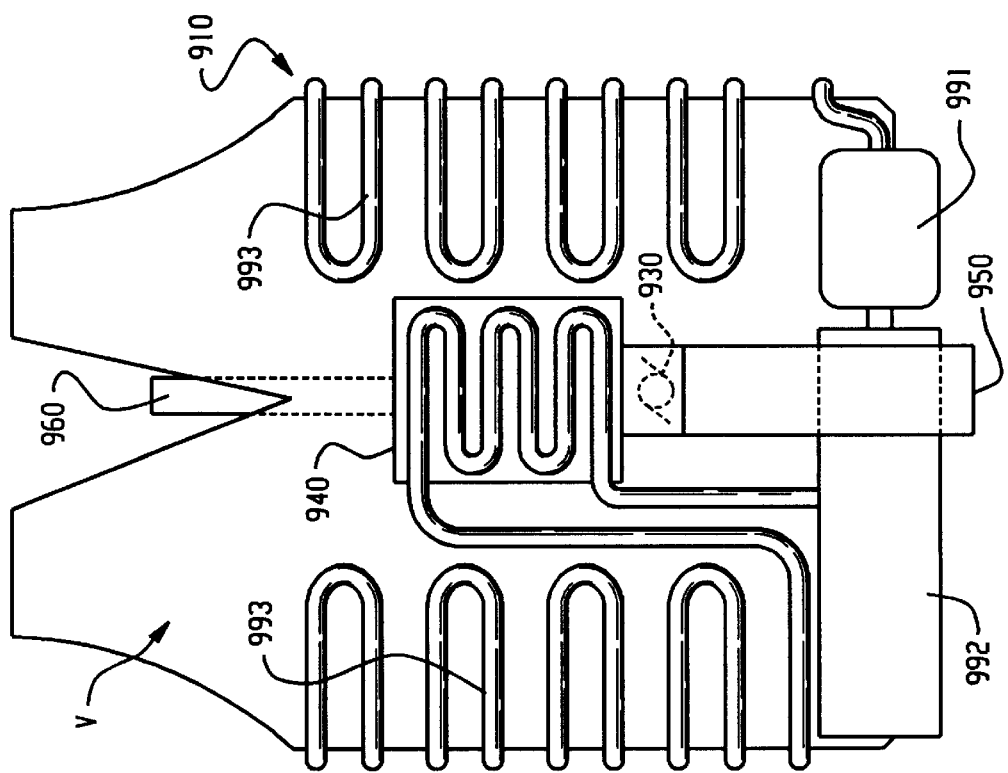
FIG. 26 is a schematic view of another embodiment of a device according to the subject invention.

FIG. 26 illustrates another embodiment of the device according to the present invention. Device 910 is adapted for use in a circulatory vest (V) that uses cold water pumped through the vest for cooling. Battery-powered water pump 991 pumps cold water through ice chamber 992 and circulatory hose 993 that is coiled through the vest, including the air cooling chamber 940. In this embodiment, ambient air drawn into the air cooling chamber 940 through intake hose 950 by fan 930 and then delivered from the air cooling chamber 940 through outake hose 960. The ambient air passing through the air cooling chamber 940 is thus cooled as it passes over the circulatory hose 993 within the chamber. In addition, the wearer of circulatory vest (V) receives cooling comfort by virtue of indirect contact with circulatory hose 993.

Besides an electric fan, other methods of driving airflow could be used with any design. For example, a diaphragm design could be used. This would use an external air bladder attached to the torso. As the wearer breathes in, his chest expands and compresses the air bladder, which in turn expels air through the cooling system. As the wearer breathes out, his chest contracts, allowing the air bladder to expand back to its normal size, thus filling with air. One-way valves in the input and output of the air bladder control the air's direction.

Inasmuch as the present invention is subject to variations, modifications and changes in detail, some of which have been expressly stated herein, it is intended that all matter described throughout this specification or shown in the accompanying drawings be considered illustrative and not limiting the scope of the invention. It should thus be evident that a device constructed in accordance with the concept of the present invention, or substantially equivalent thereto, will accomplish the objects of this invention.

What is claimed is:

1. A device for cooling a person, comprising:
   an air intake channel;
   a vacuum source for drawing ambient air into the intake channel;
   at least one gel pak for cooling the ambient air drawn into the input channel, the gel pak being in fluid communication with the input channel; and
   a cool air distribution channel in fluid communication with the input channel for distributing the cooled air in the vicinity of the person.

2. The personal cooling device according to claim 1 wherein the at least one gel pak comprises a plurality of cells joined together in a predetermined arrangement.

3. The personal cooling device according to claim 2 wherein each cell has at least one ribbed surface.

4. The personal cooling device according to claim 2 wherein each cell has at least one surface having a serpentine channel.

5. The personal cooling device according to claim 1 further comprising a plurality of temperature conduction rods in thermal communication with the at least one gel pak.

6. The personal cooling device according to claim 5 wherein the temperature conduction rods are maintained in a stacked arrangement characterized such that two adjacent rods are perpendicular to one another.

7. The personal cooling device according to claim 5 wherein the temperature conduction rods are supported by a plurality of temperature conduction plates.

8. The personal cooling device according to claim 1 wherein the at least one gel pak is in indirect contact with the person.

9. The personal cooling device according to claim 1 further comprising means for fastening the device to a costume.

10. The personal cooling device according to claim 1 wherein the vacuum source is a fan.

11. The personal cooling device according to claim 10 wherein the fan operates at a plurality of speeds.

12. The personal cooling device according to claim 10 wherein the fan is powered by a plurality of batteries.

13. The personal cooling device according to claim 10 wherein the fan is controlled by a thermostat.

14. The personal cooling device according to claim 1 wherein the vacuum source is an external air bladder.

15. The personal cooling device according to claim 1 wherein the device is mounted in a mascot costume.

16. The device according to claim 15 further comprising means for removing warm air from the costume.

17. The device according to claim 1 wherein the device is mounted to a vest.

18. The device according to claim 17 wherein the device is mounted to a plurality of shoulder straps by attachment means.

19. The device according to claim 1 wherein the device is mounted to a mask.

20. The device according to claim 19 further comprising a plurality of thermal conduction coils which cooperate with the at least one gel pak for cooling the ambient air.

21. The device according to claim 1 wherein the device is adapted for use with a cool air suit.

22. The device according to claim 1 wherein the device is adapted for use with a sun visor.

23. A method for cooling a person wearing a costume comprising the steps of:
   drawing ambient air through an intake channel;
   cooling the air below ambient temperature with a cooling source comprising a pel pak contained within the costume and in fluid communication with the intake channel; and
   delivering the cooled air to a desired area adjacent the person to provide comfort.

24. The method according to claim 23 further comprising the step of placing the cooling source in indirect contact with the person.

* * * * *